United States Patent [19]

Logothetis et al.

[11] Patent Number: 5,288,375
[45] Date of Patent: * Feb. 22, 1994

[54] METHOD FOR DETERMINING RELATIVE AMOUNT OF OXYGEN CONTAINING GAS IN A GAS MIXTURE

[75] Inventors: Eleftherios M. Logothetis, Birmingham; Richard E. Soltis, Redford, both of Mich.

[73] Assignee: Ford Motor Company, Dearborn, Mich.

[*] Notice: The portion of the term of this patent subsequent to Sep. 17, 2008 has been disclaimed.

[21] Appl. No.: 901,315

[22] Filed: Jun. 19, 1992

Related U.S. Application Data

[60] Division of Ser. No. 465,592, Jan. 18, 1990, Pat. No. 5,145,566, which is a continuation of Ser. No. 251,622, Sep. 30, 1988, abandoned.

[51] Int. Cl.$^5$ .................................. G01N 27/419
[52] U.S. Cl. .................. 204/153.18; 204/153.22; 204/425; 204/426
[58] Field of Search ............... 204/153.22, 153.18, 204/421–429

[56] References Cited

U.S. PATENT DOCUMENTS

| Re. 31,916 | 6/1985 | Oswin et al. ............... 204/153.2 |
| 3,208,926 | 9/1965 | Eckfeldt ............... 204/409 |
| 4,272,329 | 6/1981 | Hetrick et al. . |
| 4,272,330 | 6/1981 | Hetrick . |
| 4,272,331 | 6/1981 | Hetrick . |
| 4,288,775 | 9/1981 | Bennewitz et al. . |
| 4,456,902 | 6/1984 | Komine et al. . |
| 4,487,680 | 12/1984 | Logothetis et al. . |
| 4,497,701 | 2/1985 | Murata et al. . |
| 4,498,968 | 2/1985 | Yamada et al. . |
| 4,502,939 | 3/1985 | Holfelder et al. ............... 204/429 |
| 4,547,281 | 10/1985 | Wang et al. . |
| 4,568,443 | 2/1986 | Asayama et al. . |
| 4,574,627 | 3/1986 | Sakurai et al. ............... 204/425 |

(List continued on next page.)

OTHER PUBLICATIONS

"High Temperature Oxygen Sensors Based On Electrochemical Oxygen Pumping", E. M. Logothetis and R. E. Hetrick, *Fundamentals and Applications of Chemical Sensors,* 1986, American Chemical Society.
"Closed Loop Control of the EGR Rate Using the (List continued on next page.)

*Primary Examiner*—T. Tung
*Attorney, Agent, or Firm*—Lorraine S. Melotik; Roger L. May

[57] ABSTRACT

The electrochemical device and method measures the relative amount of a measurement gas consisting essentially of at least one oxygen containing gas in a gas mixture containing at least a second oxygen containing gas which is capable of being pumped out or disassociated at a voltage less than that which is capable of disassociating the measurement gas. The mixture may comprise, e.g., $O_2$, $CO_2$, and $H_2O$. Two electrochemical pump cells and a support structure form a restricted volume in communication through an aperture to the gas mixture. The device comprises a first external electrical circuit means across a first pump cell for applying a voltage to cause molecules of substantially all second oxygen containing gas molecules inside the restricted volume to be pumped out from the restricted volume or disassociated. The device also comprises a second external electrical circuit means across a second pump cell causes for applying a voltage to disassociate only of substantially all measurement gas molecules inside the volume. The device further comprises a third external electrical circuit means to measure the current flowing in the second pump cell, this current being proportional to the relative amount of measurement gas in the gas mixture. The invention also is directed to a planar electrochemical device and method for measuring the relative percentage of a measure gas in a gas mixture like that described above.

4 Claims, 4 Drawing Sheets

U.S. PATENT DOCUMENTS

| | | |
|---|---|---|
| 4,578,172 | 3/1986 | Yamada et al. |
| 4,579,643 | 4/1986 | Mase et al. .......................... 204/424 |
| 4,582,657 | 4/1986 | Shibata et al. |
| 4,614,175 | 9/1986 | Asayama |
| 4,645,572 | 2/1987 | Nishizawa et al. |
| 4,658,790 | 4/1987 | Kitahara |
| 4,718,999 | 1/1988 | Suzuki et al. ....................... 204/426 |
| 4,722,779 | 2/1988 | Yamada et al. ..................... 204/426 |
| 4,765,880 | 8/1988 | Hayakawa et al. ................. 204/425 |
| 4,769,124 | 9/1988 | Okada et al. ........................ 204/425 |
| 4,770,760 | 9/1988 | Noda et al. .......................... 204/426 |
| 4,851,103 | 7/1989 | Usami et al. ........................ 204/425 |
| 5,145,566 | 9/1992 | Logothetis et al. ................. 204/426 |

OTHER PUBLICATIONS

Oxygen Sensor", M. Nishida, N. Inoue, H. Suzuki, and S. Kumasgai, SAE International Congress and Exposition, Feb. 29–Mar. 4, 1988, Technical Paper No. 880133.

"Humidity Sensing Properties Of The Limiting Current Type Oxygen Sensor", Toshio Usui and Yoichi Kurumiya, *Transducers* '87, pp. 701–704.

METHOD FOR DETERMINING RELATIVE AMOUNT OF OXYGEN CONTAINING GAS IN A GAS MIXTURE

This is a division of application Ser. No. 07/465,592, file on Jan. 18, 1990, now U.S. Pat. No. 5,145,566, which is a file wrapper continuation of Ser. No. 07/251,622, filed Sep. 30, 1988, now abandoned.

Reference is made to U.S. application Ser. No. 55,821 to Logothetis et al filed May 29, 1987 U.S. Pat. No. 5,049,254 and entitled "Exhaust Gas Recirculation Sensor and Method" which disclosed related subject matter.

FIELD OF THE INVENTION

This invention relates to a device and method for determining the relative amount of an oxygen containing gas (hereafter called "measurement gas") in a gas mixture comprising at least one other oxygen containing gas, e.g., a humidity sensor for determining the amount of water vapor in air.

DISCUSSION OF THE RELATED ART

Humidity sensors are of considerable usefulness in a variety of applications. For example, humidity sensors have been used for environmental control in computer rooms, commercial aircraft and automobiles. They are also useful in automotive and aircraft systems for carburetion control. A humidity sensitive device is typically structured such that opposing electrodes are formed on an insulating substrate and a humidity sensitive film is formed on the surface of the insulating substrate and at least between the opposing electrodes. The humidity sensitive film comprises a material exhibiting a predetermined humidity-resistance value characteristic. Accordingly, the inherent resistance value of the humidity sensitive film is variable as a function of an ambient humidity and as a result, a humidity condition can be determined in terms of a resistance value of the humidity sensitive device. Exemplary of the humidity sensitive film are organic materials such as cellulose and metal oxides such as aluminum oxide. Exemplary of devices of this type are those disclosed in U.S. Pat. Nos. 4,288,775; 4,456,902; and 4,497,701. Unfortunately, however, prior art humidity sensors are less than desirable for automotive use for one or more of the following reasons: poor reliability, lack of durability, complexity and cost.

In the last 20 years, several different types of sensors based on $O_2$-pumping $ZrO_2$ cells have been developed. Such oxygen-pumping is based on the fact that if a current is passed through an oxygen ion-conducting electrolyte (e.g., zirconia), oxygen is transferred (pumped) from one side of the electrolyte to the other. The oxygen may come from oxygen gas or gaseous compounds containing oxygen, e.g., $H_2O$, that are disassociated at the electrolyte. Such sensors have the common characteristic that their signal output is linearly proportional to the partial pressure of the oxygen transferred. As discussed, e.g., in "High Temperature Oxygen Sensors Based on Electrochemical Oxygen Pumping", E. M. Logothetis and R. E. Hetrick, *Fundamentals and Applications of Chemical Sensors*, 1986, American Chemical Society, the sensors may be of the single or double cell type.

In single-cell sensors, the same $ZrO_2$ cell is used for both oxygen pumping and sensing. In double-cell sensors, different $ZrO_2$ cells are used for oxygen pumping and sensing. U.S. Pat. No. 4,547,281 to Wang is directed to a single cell device capable of sensing the concentration of oxygen in a volume. Double cell sensors capable of sensing the concentration of oxygen in a volume are disclosed, e.g., in U.S. Pat. Nos. 4,272,329, 4,272,330, and 4,272,331 to Hetrick and Hetrick et al; U.S. Pat. No. 4,498,968 to Yamada et al; U.S. Pat. No. 4,645,572 to Nishizawa et al; and U.S. Pat. No. 4,487,680 to Logothetis et al. The Hetrick, Hetrick et al and Logothetis et al patents are commonly assigned with this invention. In general, in these two cell devices, one cell is used to pump a certain (variable) amount of $O_2$ out of a cavity formed between the cells and the second cell (the sensor cell) is used to measure the reduced partial pressure of $O_2$ inside the cavity. As described in the patent to Logothetis et al, the structure of that device has been modified to eliminate the cavity and employs only three electrodes, instead of the common four, but operates analogously to those of the '329, '330 and '331 patents discussed above.

Oxygen sensors based on oxygen-pumping are able to measure the amount of $O_2$ in a mixture comprising another oxygen containing gas such as $H_2O$, because oxygen is pumped out at a voltage lower than that required to disassociate the other oxygen containing gas ($H_2O$). Such prior devices, however, were not able to determine the percentage of $H_2O$ in an $O_2/H_2O$ gas mixture unless the concentration of the other oxygen containing gas is known or its concentration remains fixed. Such prior art devices cannot be used to measure the concentration of $H_2O$ in an $O_2/H_2O$ gas mixture if the amount of $O_2$ is variable because, if a voltage is applied to a pump cell sufficient to disassociate the $H_2O$, the $O_2$ interferes. That is, the $O_2$ is pumped out at a voltage lower than that required to disassociate $H_2O$. The concentration which could be determined in this instance would be the combined concentration of $O_2 + H_2O$. Similarly, in a $CO_2/H_2O$ gas mixture having variable amounts of these gases, the concentration of $H_2O$ can not be determined using the technology of prior art devices because if a voltage is applied across the pump cell sufficient to disassociate the $H_2O$, the $CO_2$ would similarly be disassociated. Thus, the concentration which could be determined in this instance would be the combined concentration of $CO_2 + H_2O$.

It would be desirable to have a device capable of measuring the relative amount of one oxygen containing gas, e.g. $CO_2$ or $H_2O$ in a gas mixture comprising variable amounts of, e.g., $O_2$, $CO_2$, $H_2O$, and $N_2$. It would further be desirable if this device had good reliability and were durable for use in automotive applications, i.e., in a high temperature environment, not be complex and be reasonable in cost. The present invention describes a method and device for measuring the relative amount of an oxygen containing gas in a mixture of "interfering" oxygen containing gases which overcomes the deficiencies of prior art devices and is well suited for use as an automotive humidity sensor.

Embodiments of the device of the present invention are similar to the two cell devices in that they comprise two solid electrochemical oxygen pump cells, which may define a cavity between them or be similar to the structure of the Logothetis et al patent discussed above. The present invention device, however, does not use one cell for oxygen-pumping and the second for oxygen-sensing as in the two cell devices described above.

Rather, the invention claimed herein uses both cells as $O_2$-pumping cells.

In commonly assigned U.S. application Ser. No. 55,821 to Logothetis et al filed May 29, 1987 and entitled "Exhaust Gas Recirculation Sensor and Method", a device and method is disclosed for measuring the relative amount of exhaust gas recirculation (EGR) in a combined intake air and exhaust gas mixture of an internal combustion engine (termed the "ambient atmosphere"). This invention relates to a device which uses both cells as $O_2$-pumping cells. In one embodiment of that device, two oxygen pump cells are arranged so that, with them, a restricted volume is defined, the volume being linked to the ambient atmosphere through an aperture. A first external circuit means is coupled across the first pump cell to apply a constant voltage across the first cell so that all oxygen molecules are pumped out of the volume. A second external circuit means is coupled to the second pump cell to apply a constant voltage across the second pump cell so that all $CO_2$ and $H_2O$ molecules in the volume are disassociated. A third external circuit means is coupled to the second pump cell to measure a current flowing through the second pump cell. Since the current flowing through the second pump cell is directly related to the amount of ($CO_2$+$H_2O$) molecules which are disassociated, the current is proportional to the relative amount of $CO_2$ plus $H_2O$ in the ambient atmosphere. For engines controlled at the stoichiometric air-fuel ratio, the relative amounts of ($CO_2$+$H_2O$) in the ambient atmosphere can be related to the amount of EGR. Thus, knowing the relative amount of ($CO_2$+$H_2O$) in the ambient atmosphere by means of that device, the EGR can be determined.

The device disclosed herein comprises similar structure configuration and circuitry as in U.S. application Ser. No. 55,821 described above. That application, however, does not disclose a method or device for measuring the relative amount of only one oxygen containing gas, e.g., only the $CO_2$ or only the $H_2O$ as is possible according to the present invention.

As described above, the device of U.S. application Ser. No. 55,821 determines the relative amount of the combination of two oxygen containing gases, in particular, $CO_2$+$H_2O$, in a gas mixture further comprising oxygen. This can also be done by the present invention. Advantageously, however, according to embodiments of the present invention the relative amount of a single oxygen containing gas in a gas mixture can be determined, even when the mixture contains variable amounts of each of the gases. Thus, while according to the present invention the relative amount of, e.g., ($CO_2$+$H_2O$) in an $O_2$, $CO_2$, and $H_2O$ gas mixture can be determined as in the invention of '821 discussed above, advantageously the relative amount of, e.g., $CO_2$ and the relative amount of $H_2O$ can also be individually determined in a $O_2/CO_2/H_2O$ gas mixture, even if the mixture contains variable amounts of each of the gases.

SUMMARY

This invention is directed to an electrochemical oxygen pumping device for measuring the relative amount of a measurement gas consisting essentially of at least one oxygen containing gas in a gas mixture comprising in addition at least a second oxygen containing gas which is capable of being pumped out from the device or disassociated at a voltage less than that which is capable of disassociating the measurement gas. The electrochemical device comprises a first solid electrochemical oxygen pump cell having a first pair of opposed electrodes and a second electrochemical oxygen pump cell having a second pair of opposed electrodes. A supporting structure is coupled to the first and second pump cells to form with them a restricted volume. The device comprises at least one aperture for providing communication between the restricted volume and the gas mixture. The device further comprises a first external electrical circuit means coupled to the first pump cell for applying a first voltage across the first pump cell to negatively bias a first pump cell electrode of the first pair of opposed electrodes inside the restricted volume (i) sufficiently to cause substantially all the second oxygen containing gas molecules inside the restricted volume to be pumped out from the restricted volume or disassociated by a current flowing through the first pump cell and (ii) insufficiently to disassociate the measurement gas. The device also comprises a second external electrical circuit means coupled to the second pump cell for applying a second voltage across the second pump cell to negatively bias a second pump cell electrode of the second pair of opposed electrodes inside the volume sufficiently to disassociate only substantially all the measurement gas inside the restricted volume by a current flowing through the second pump cell. Additionally, the device comprises a third external electrical circuit means coupled to the second pump cell to measure the current flowing through the second pump cell, the second pump cell current being proportional to the relative amount of the measurement gas in the gas mixture.

This invention is thus capable of measuring the relative amount of one oxygen containing gas in a gas mixture containing at least one other oxygen containing gas. This invention is also capable of measuring the total relative amount of two or more oxygen containing gases in a gas mixture containing at least one other oxygen containing gas. Herein "measurement gas" may be used to denote one or more such gases whose relative amount is being measured.

According to another aspect of the invention, a method is disclosed herein using the electrochemical oxygen pumping device disclosed above for measuring the relative amount of measurement gas in a gas mixture, which gas mixture has been described above. The method comprises providing communication between the gas mixture and the restricted volume of the electrochemical device and applying a first voltage across the first pump cell to negatively bias a first pump cell electrode of the first pair of opposed electrodes inside the restricted volume (i) sufficiently to cause substantially all the second oxygen containing gas molecules inside the restricted volume to be pumped out from the restricted volume or disassociated by a current flowing through the first pump cell and (ii) insufficiently to disassociate the measurement gas. The method further comprises applying a second voltage across the second pump cell to negatively bias a second pump cell electrode of the second pair of opposed electrodes inside the restricted volume sufficiently to disassociate only substantially all the measurement gas inside the restricted volume by a current flowing through the second pump cell. That is, the second voltage is sufficient to disassociate the measurement gas but is less than that capable of disassociating oxygen containing gases which require a higher voltage for their disassociation. The method also comprises measuring the current flowing through the second pump cell, the second pump cell current being proportional to the relative amount of the measurement gas in the gas mixture.

This invention in another aspect is directed to an electrochemical oxygen pumping device for measuring the relative amount of a measurement gas consisting essentially of at least one oxygen containing gas in a gas mixture comprising in addition at least a second oxygen containing gas which is capable of being pumped out of the device or disassociated at a voltage less than that which is capable of disassociating the measurement gas. This electrochemical device comprises a generally planar first electrochemical oxygen pump cell including a relatively dense platelet with one of a pair of porous electrodes on each of two spaced sides of the platelet; a first porous layer deposited on one electrode of the first pump cell; a generally planar second electrochemical oxygen pump cell including a first porous electrode, a second porous layer and a second porous electrode deposited successively on the first porous layer; a second cell external electrical circuit means coupled to the second pump cell for applying a first voltage across the second pump cell to positively bias the second electrode (i) sufficiently to cause substantially all the second oxygen containing gas molecules inside the first porous layer to be pumped out or disassociated by a current flowing through the second pump cell and (ii) insufficiently to disassociate the measurement gas; a first cell external electrical circuit means coupled to the first pump cell for applying a second voltage across the first pump cell to positively bias the exposed electrode of the first pump cell sufficiently to disassociate only substantially all of the measurement gas molecules inside the first porous layer; and a third external electrical circuit means coupled to the first pump cell to measure the current flowing through the first pump cell, the current being proportional to the relative amount of the measurement gas in said gas mixture. This device may be termed herein as a "planar electrochemical device".

According to yet another aspect of the invention, it is directed to a method of using the planar electrochemical device disclosed above to measure the relative amount of a measurement gas in a gas mixture, which gas mixture has been described above. The method comprises providing communication between the gas mixture and the first porous layer of the planar electrochemical device, applying a first voltage across the second oxygen pump cell to positively bias the second electrode (i) sufficiently to cause substantially all the second oxygen containing gas molecules inside the first porous to be pumped out or disassociated by a current flowing through the second pump cell and (ii) insufficiently to disassociate the measurement gas; applying a second voltage across the first oxygen pump cell to positively bias the exposed electrode of the first pump cell sufficiently to disassociate only substantially all of the measurement gas molecules inside the first porous layer; and measuring the current flowing through the first pump cell, the current being proportional to the relative amount of the measurement gas in the gas mixture.

According to one embodiment of this invention, the device (in any of the aspects disclosed above) can be used as a humidity sensor for any gas mixture containing at least $H_2O$ and another oxygen containing gas. When used as a humidity sensor, the device and method determine the relative amount of water vapor (absolute humidity) in the gas mixture, e.g., air. Relative humidity can be determined by also employing a thermistor to measure the temperature. According to another aspect of this invention, the relative amount of $H_2O$ gas in an exhaust gas/intake air mixture of an internal combustion engine can be determined and used as a measure of EGR in the mixture, i.e., the device could function as an EGR sensor. A correction for the humidity in the air could be made by using the device to measure the $H_2O$ for zero EGR, i.e., as a humidity sensor for the intake air. Still other aspects of the invention will be apparent in view of the detailed disclosure below.

The device and method of this invention can be used in a continuous way (i.e., to continuously monitor the relative amount of an individual gas or a combination of gases in a gas mixture) or in an intermittent (sampling) way. That is, the values of the appropriate individual voltages across the first and second pump cells may be maintained for an extended period of time during which it is desired to continuously measure the relative amount of the measurement gas in the restricted volume, e.g., the humidity in air during the entire operation of an automobile. On the other hand, the determination of the relative amount of the measurement gas need not be done continuously. Measurement of e.g., the humidity of air, can be done on a periodic basis. If it is desired to determine the concentration of $CO_2$ in the air and also to determine the humidity of the same air sample, the voltages across the first and second pump cells would be alternated, first to that combination which will allow measurement of the $CO_2$ in the air sample (which will be described hereafter in greater detail) and then to that combination which will allow measurement of the humidity ($H_2O$) in the air (as also will be described in greater detail hereafter). In either case, the measurement of the current across the second pump cell would take place during the time the electrodes are energized, as will be apparent to those skilled in the art in view of the present disclosure.

The device of the present invention when used, e.g., as a humidity sensor, has characteristics which offer advantages over prior art humidity sensors. For example, it provides stable operation since the components are not subject to the aging characteristics of e.g., $Al_2O_3$, whose capacitance and resistivity change with time.

DETAILED DESCRIPTION OF THE PREFERRED EMBODIMENTS

Figure 1:
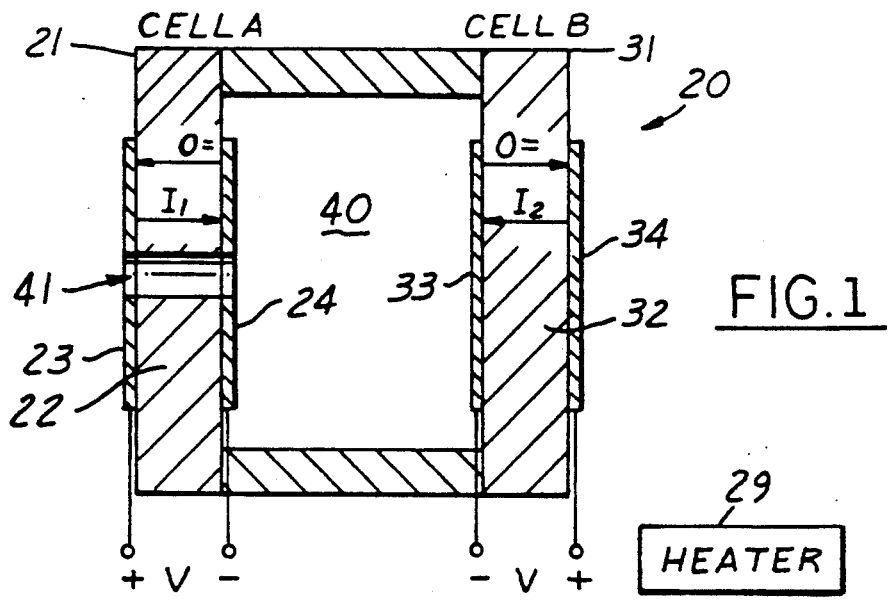
FIG. 1 is a schematic of an electrochemical device for measuring the relative amount of a measurement gas in a gas mixture according to one embodiment of the present invention.

This invention is directed to an electrochemical oxygen pumping device and method for determining the relative amount of a measurement gas consisting essentially of at least one oxygen containing gas in a gas mixture comprising in addition at least a second oxygen containing gas which is capable of being pumped out of the device or disassociated at a voltage less than that which is capable of disassociating the measurement gas. One embodiment of the device is shown in FIG. 1. This device 20 has two electrochemical cells 21 and 31 arranged with a supporting structure so that a restricted volume 40 is defined. Volume 40 communicates with a gas mixture (e.g., $O_2$, $H_2$, and $H_2O$) through at least one aperture 41. Each of the two cells consists of a platelet 22, 32 made from an oxygen ion conducting solid electrolyte such as $ZrO_2$, and two electrodes 23, 24, 33, 34 applied on the two sides of the platelets. These electrodes are made from platinum or some other material according to procedures well established in the area of oxygen sensors. Electrochemical cells 21 and 31 are operated as oxygen pumps having currents $I_1$ and $I_2$ passing through them when appropriate voltages are applied across each cell. Advantageously, a heater 29 is positioned adjacent sensor 20 to provide an elevated temperature of about at least 500° C. suitable for operation of sensor 20.

Figure 4A:
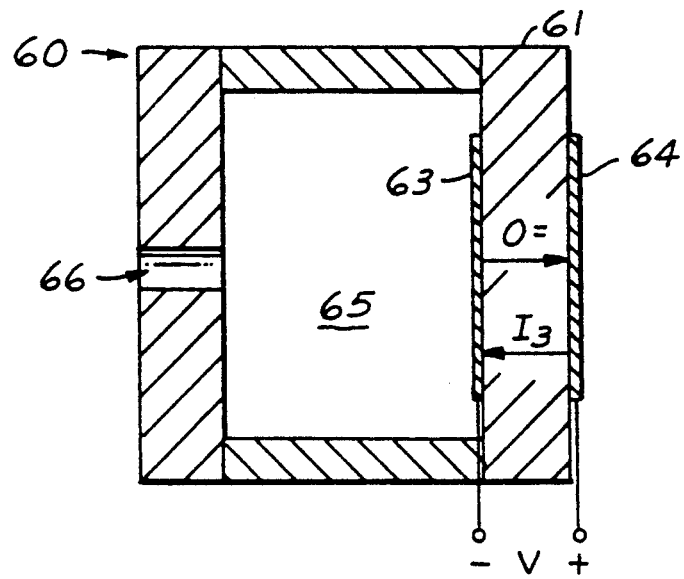
FIG. 4A is a schematic of a single-cell oxygen pumping device according to the prior art.

In order to more fully understand the operation of device 20, first consider a single $ZrO_2$ device 60 of FIG. 4A well known in the art for use in sensing oxygen gas ($O_2$) percentage in the intake air/exhaust mixture of internal combustion engines. Operation of this prior art type of device is based on oxygen pumping. It has a single $ZrO_2$ cell 61 made from a $ZrO_2$ platelet with two platinum electrodes 63 and 64 arranged in a structure so that a volume 65 is defined. Volume 65 communicates with a gas mixture comprising $O_2$, e.g., an intake air/exhaust gas mixture of an internal combustion engine, through an aperture 66. When a voltage is applied across cell 61 so that electrode 63 is negative, a current $I_3$ passes through the $ZrO_2$ material as a result of a motion of oxygen ions from electrode 63 to electrode 64.

As the oxygen ions formed at electrode 63 travel through the $ZrO_2$ platelet to electrode 64, more $O_2$ molecules from the gas phase disassociate and react with electrons at electrode 63 to form oxygen ions ($O^=$). By means of this electrochemical reaction, as oxygen ions are depleted at electrode 63 (in traveling to electrode 64) more oxygen ions are formed from $O_2$ gas molecules in volume 65. By means of an inverse electrochemical reaction, oxygen ions at electrode 64 are released as $O_2$ molecules into the ambient gas. The net effect of the current through the cell is to pump $O_2$ out of volume 65. Because of the lower concentration of $O_2$ inside volume 65, there will be a diffusional flux of $O_2$ from the gas mixture (e.g., intake air/exhaust gas mixture) into volume 65 through aperture 66. Under steady state conditions, the diffusional flux of $O_2$ into volume 65 will be equal to the flux of $O_2$ pumped out of volume 65 by the pumping current.

Figure 4B:
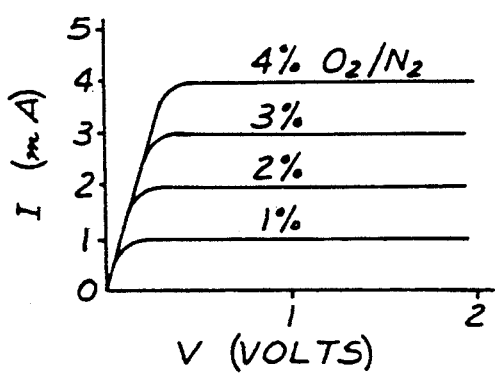
FIG. 4B is a graph showing the relation between the pumping current and the pumping voltage of the oxygen pumping device of FIG. 4A in $O_2/N_2$ gas mixtures.
Figure 4C:
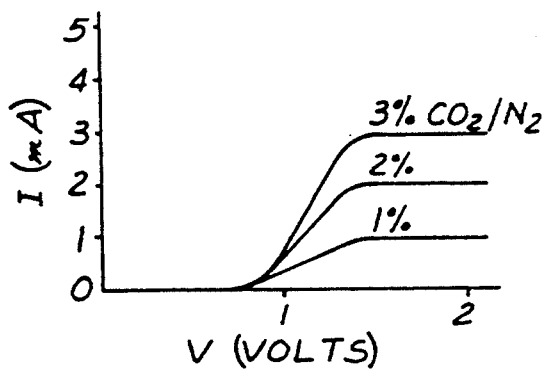
FIG. 4C is a graph showing the relation between the pump current and the pumping voltage of the oxygen pumping device of FIG. 4A in $CO_2/N_2$ gas mixtures.
Figure 4D:
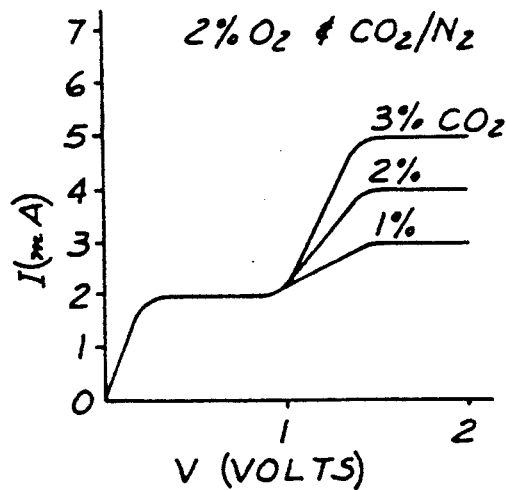
FIG. 4D is a graph showing the relation between the pumping current and the pumping voltage of the oxygen pumping device of FIG. 4A in $O_2/CO_2/N_2$ gas mixtures.
Figure 5:
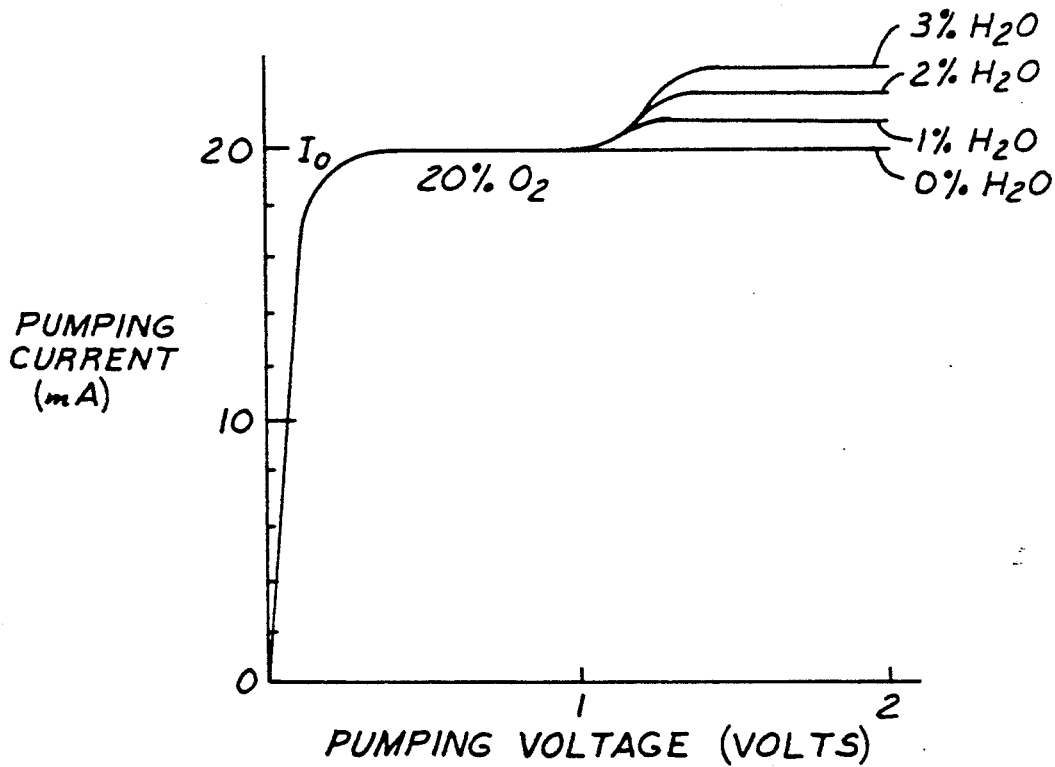
FIG. 5 is a graph showing the relation between the pumping current and the pumping voltage of the prior art oxygen pumping device of FIG. 4A in $O_2/H_2O$ gas mixtures.
Figure 6:
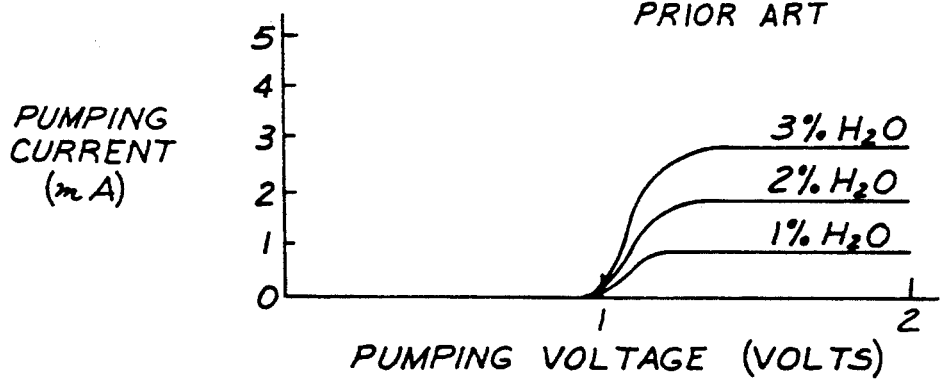
FIG. 6 is a graph showing the relation between the pumping current and the pumping voltage of the present invention oxygen pumping device of FIG. 1 in $O_2/H_2O$ gas mixtures.

In an $O_2/N_2$ mixture, the current voltage (I-V) characteristic of prior art device 60 is shown in FIG. 4B. For small voltages, the current increases with voltage as more oxygen is pumped out of volume 65. For sufficiently large voltages, the pumping current saturates. This corresponds to the condition that all oxygen inside volume 65 is pumped out by the current. The saturation current $I_s$ is proportional to the relative amount of $O_2$ in the ambient. FIG. 4C shows the I-V characteristic of sensor 60 in a $CO_2$ and $N_2$ mixture. Because of the lack of oxygen, the pumping current is zero for low voltages. Above a threshold value of about 0.7 volts, the pumping current increases with voltage due to electrodisassociation of $CO_2$. For still higher voltages, saturation currents are again observed corresponding to the disassociation of all $CO_2$ inside volume 65. The saturation current is proportional to the relative amount of $CO_2$ in the gas. A similar I-V characteristic is obtained with $H_2O/N_2$ mixtures except that the threshold voltage for the disassociation of $H_2O$ is somewhat larger (about 1.1 volt). It is apparent that the prior art device of FIG. 4A can be used to measure the total concentration of oxygen containing gases, e.g., $O_2$, $H_2O$, and $CO_2$, in a gas mixture additionally containing inert gases (i.e., non-oxygen containing gases), e.g. $N_2$. This can be done by applying a sufficiently large voltage to achieve complete disassociation of all of the oxygen containing gases. FIG. 4D shows the I-V characteristic of prior art device 60 in $O_2$, $CO_2$, and $N_2$ gas mixtures, in particular for a mixture containing a fixed concentration of $O_2$ (2%) and variable concentrations of $CO_2$. The saturation current observed at lower voltages (V<1 volt) corresponds to the complete removal of $O_2$ from inside volume 65; the saturation current obtained at the higher voltage (V>1.1 volts) is proportional to the concentration of $O_2$ plus $CO_2$ in the mixture. FIG. 5 shows the I-V characteristics of prior art device 60 in gas mixtures comprising a fixed concentration of $O_2$ (20%) and variable amounts of $H_2O$ as may be present in air. The saturation current $I_s$ is proportional to the concentration of $O_2$ plus $H_2O$ in the mixture. However, since the concentration of the $O_2$ remains fixed, the relative amount of the $H_2O$ in the gas mixture could be determined from the value of the saturation current, whose variation would be due then to the varying concentration of the $H_2O$ as seen in FIG. 5. Toshio Usui and Yoichi Kurumiya in "Humidity Sensing Properties Of The Limiting Current Type Oxygen Sensor", *Transducers '87*, pp. 701-704, disclose an oxygen sensor of the single-cell $ZrO_2$ type similar to prior art device 60 shown in FIG. 4A. This reference discloses I-V characteristics for gas mixtures of $O_2$, $N_2$ and $O_2$, and $H_2O$.

Device 60 of FIG. 4A cannot be used, however, to determine the relative amount of one oxygen containing gas, such as $H_2O$, in a gas mixture containing at least one other oxygen containing gas, such as $O_2$, when a variable amount of $O_2$ exists in the gas mixture. In such a situation, the saturation current would be proportional to the total concentration of $O_2+H_2O$. Since both concentrations are variable, using such a prior art device, one could not determine what proportion of the saturation current was due to each gas individually.

The measurement of the relative amount of a gas, e.g., $H_2O$, in a mixture comprising at least one other oxygen containing gas, e.g., $O_2$ can be accomplished, however, with device 20 of FIG. 1, an embodiment of the present invention. For a gas mixture consisting essentially of $O_2$, $H_2O$, a constant voltage of less than 0.8 volts, and advantageously in the range of 0.2 to 0.8 volts, is applied across cell 21 so that electrode 24 is negative to pump all $O_2$ out of volume 40. A second constant voltage larger than about 1.0 volts, and advantageously in the range of 1.2 to 2.0 volts is applied across cell 31 so that electrode 33 is negative to disassociate all $H_2O$ inside volume 40. The current $I_2$ through cell 31 is proportional to the $H_2O$ concentration in the gas mixture. If the gas mixture were to comprise $O_2$, $CO_2$, and $H_2O$ and it were desired to again measure the $H_2O$ concentration, a constant voltage greater than 0.7 volts but less than about 1.0 volts (i.e. the voltage necessary to pump out all $O_2$ and disassociate all $CO_2$ without disassociating $H_2O$) would be applied across cell 21 with electrode 24 being made the negative electrode. A second constant voltage larger than about 1.0 volts, and advantageously in the range of 1.3 to 2.0 volts, is applied across cell 31 so that electrode 33 is negative to disassociate all the $H_2O$ in the volume 40. The current $I_2$ through cell 31 is proportional to the $H_2O$ concentration in the gas mixture.

As described above, the gas mixture comprises at least two oxygen containing gases. The oxygen containing gases can be selected from the group consisting essentially of oxygen, $O_2$, and oxygen containing gas compounds such as $NO_2$, $CO_2$, $H_2O$, $SO_2$, $CO$, etc. Exemplary of gas mixtures which may be employed according to the invention are $O_2$ and $H_2O$; $O_2$, $H_2$ and $H_2O$; $H_2O$ and $CO_2$; $H_2O$, $CO_2$, $N_2$ and $CO$; $O_2$, $CO_2$ and $H_2O$; $O_2$, $N_2$ and $H_2O$; $O_2$, $N_2$ and $CO_2$; $O_2$ and $CO_2$; air; and the like. Still other gas mixtures which may be employed in the present invention device and method will be apparent to those skilled in the art in view of the present disclosure.

If the gas mixture employed in the invention is selected from a gas mixture comprising $H_2O$ in addition to at least one other oxygen containing gas, the device can function as a humidity sensor. That is, the device can be used to determine the relative amount of water vapor ($H_2O$) in the gas mixture. During practice of the invention, oxygen containing gases which can be pumped out of the device or disassociated at a voltage lower than that required to disassociate any measurement gas, e.g., $H_2O$, will be pumped out or disassociated by first pump cell 21. Accordingly, in the first six gas mixtures disclosed in the previous paragraph, if the device is used to measure humidity, the following gases will be respectively pumped out or disassociated at first pump cell 21: $O_2$; $O_2$; $CO_2$; $CO$ and $CO_2$; $O_2$ and $CO_2$; and $O_2$. Since, according to the invention the measurement gas is disassociated by the second cell, in these mixtures, the voltage applied across second pump cell 31 would be that sufficient to disassociate substantially all of the $H_2O$ molecules. As mentioned above, the humidity ($H_2O$ content) of air as measured by the present device is the absolute humidity. Relative humidity can be determined by further employing a thermistor to measure the temperature.

Should it be desired to measure, e.g., $CO_2$ in a $O_2$, $CO_2$ and $H_2O$ gas mixture, a voltage sufficient to pump out $O_2$ at first pump cell 21 would be applied and a voltage sufficient to disassociate $CO_2$ (but less than that which will disassociate $H_2O$) would be applied across the second pump cell 31. The device may be employed, e.g., to maintain a desired relative amount of $CO_2$ in a controlled environment. Should it be desired to determine the amount of $CO_2+H_2O$ in this gas mixture, a voltage would be applied across first pump cell 21 sufficient to pump out substantially all $O_2$ and a higher voltage, sufficient to disassociate both the $CO_2$ and $H_2O$, would be applied across second pump cell 31. This embodiment is the subject of the Logothetis et al U.S. application Ser. No. 055,821 described above.

As disclosed above, the present invention device is capable of measuring the relative amount of a measurement gas in a gas mixture. The measurement gas whose concentration is measured according to the present invention can be one or more gases selected from the gas mixture which can be disassociated at second pump cell 31 at a voltage greater than that at which the second oxygen containing gas can be pumped out or disassociated at the first pump cell 21. The second oxygen containing gas pumped out or disassociated at pump cell 21 can be one or more gases. If only one second oxygen containing gas is removed at pump cell 21 and should it be desired to additionally measure the concentration of this gas, e.g., the $O_2$ concentration in an $O_2$, $CO_2$, $H_2O$ gas mixture, currently available oxygen sensors could be used. Alternately, according to another embodiment of this invention, the sensor of this invention could be used as described above with the addition that the pumping current $I_1$ through cell 21 is also measured by suitable circuitry connected across cell 21. In this case $I_1$ is proportional to the $O_2$ concentration. According to yet another embodiment of-this invention, the sensor of this invention could be used to measure the concentration of the gas removed at cell 21 by applying voltage, $V=0$, across first pump cell 21 and then applying across second pump cell 31 a voltage sufficient to pump out the $O_2$, but less than that which will disassociate any other oxygen containing gases ($CO_2$, $H_2O$). The current generated across cell 31 being proportional to the concentration of $O_2$. In effect, using the present invention device in this second way converts it, for a time, to a single cell oxygen sensor.

Similarly, in a $CO_2$, $H_2O$ gas mixture, according to the present invention, $CO_2$ would be disassociated at first pump cell 21 and the $H_2O$ would be disassociated and its concentration measured at second pump cell 31. Should it be desired to additionally measure the concentration of $CO_2$, known oxygen sensors could be employed as described above. Alternately, according to another embodiment of this invention, the sensor of this invention could be used with the addition that the pumping current $I_1$ through cell 21 is also measured. In this case, $I_1$ is proportional to the $CO_2$ concentration. According to still another embodiment of this invention, the sensor of this invention could be used to measure the concentration of the $CO_2$ gas removed at cell 21 by applying voltage, $V=0$, across first pump cell 21 and applying a voltage across second pump cell 31 sufficient to disassociate $CO_2$ but less than that which will disassociate $H_2O$. While the discussions of this and the prior paragraph for measuring the concentration of the gas removed at pump cell 21 have been directed to device 20, it will be apparent to those skilled in the art in view of the present disclosure that this techniques can be similarly applied to the planar device of this invention.

Figure 2:
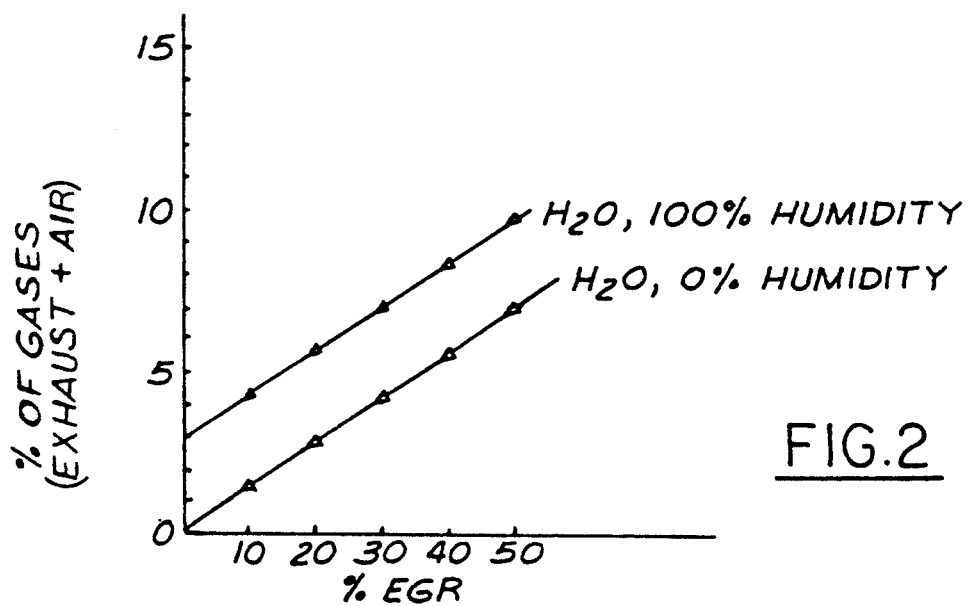
FIG. 2 is a graph relating the relative amount of $H_2O$ in a combined intake air and exhaust mixture to the relative amount of EGR.
Figure 3:
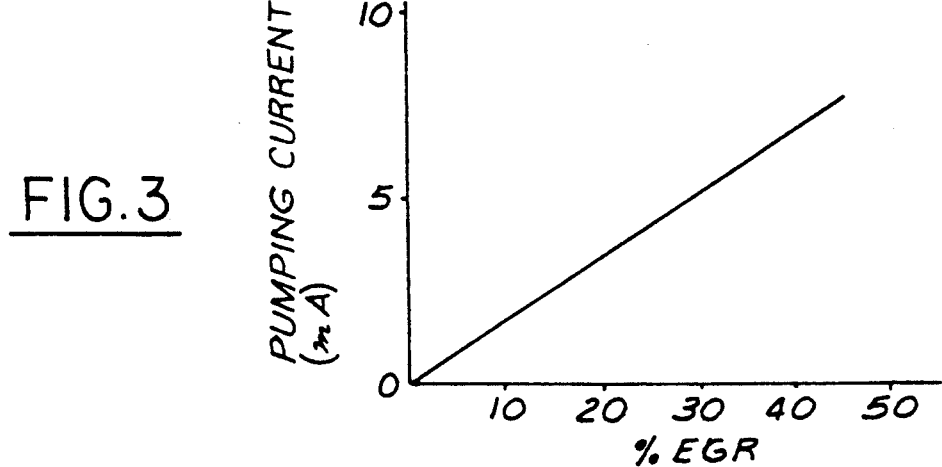
FIG. 3 is a graph showing the output of the measurement gas sensor according to the embodiment of the present invention shown in FIG. 1 as a function of EGR.

If the $O_2$, $CO_2$ and $H_2O$ mixture is an exhaust gas/intake air mixture of an internal combustion engine, this invention can be used to determine the EGR based on the relative amount of $H_2O$ in the exhaust gas/intake air mixture. As is known in the art, for an engine controlled at the stoichiometric air-to-fuel ratio, the relative amount of $H_2O$ in the exhaust gas is constant for constant humidity in the air. For example, for a fuel with hydrogen-to-carbon ratio of about 2.3 (stoichiometric A/F value equal to 14.7), the relative amount of $H_2O$ in the exhaust gas at A/F=14.7 is about 13% by volume. FIG. 2 shows the relative amount of $H_2O$ in the combined exhaust gas/intake air mixture as a function of the relative amount of EGR. FIG. 3 shows the output (pumping current of cell 31) of sensor 20 as a function of EGR. The effect of humidity in the air is indicated by showing plots for 0% and 100% humidity at a temperature of 70° F. It is apparent that the relative amount of $H_2O$ in the combined exhaust gas/intake air depends appreciably on humidity. The effect of humidity normally present in air can be eliminated by measuring the $H_2O$ for zero EGR (completely closed EGR valve), i.e., by using the device to measure the relative amount of water vapor in the air& Alternately, a second (separate) device of this type could be used to measure the relative amount of water vapor in the air in order to correct for the ambient water vapor and thus accurately determine EGR based on the relative amount of $H_2O$ in the exhaust gas/intake air mixture.

As disclosed above, this invention is capable of measuring the relative amount of a measurement gas consisting essentially of at least one oxygen containing gas in a gas mixture comprising in addition at least a second oxygen containing gas which is capable of being pumped out of the device or disassociated at a voltage less than that which is capable of disassociating the measurement gas. Accordingly, in a gas mixture containing $O_2$, A, B, and C (A, B and C being oxygen containing gases) and if $O_2$ can be pumped out at a voltage lower than that capable of disassociating A, B, and C, the relative amount of each of A, B and C in the gas mixture can individually be measured. In addition, also as disclosed above, this invention is capable of measuring the total relative amount of two or more oxygen containing gases (also termed "measurement gas") in a gas mixture containing at least a second (i.e., one additional) oxygen containing gas. For the sake of explanation, let us assume that gas A disassociates above 1.3 volts, that gas B disassociates above 1.9 volts and that gas C disassociates above 2.3 volts. According to an embodiment of this invention, in order to measure the total concentration of gases A+B, a voltage of about 0.8 volts is applied across cell 21 (electrode 24 being negative) to pump out all $O_2$ from volume 40 and a voltage of 2.2 volts is applied across cell 31 (electrode 33 being negative) to disassociate all A and B (but not C) gas molecules in volume 40. The saturation current of cell 31 would be proportional to the concentration of A plus B in the mixture. In this case, $O_2$ would be considered the second oxygen containing gas and A plus B would be considered the measurement gas. Similarly, the total concentration of A+B+C would be determined by applying a voltage of about 0.8 volts across cell 21 and a voltage of, for example, 2.6 volts across cell 31. To measure the total relative amount of B+C in the gas mixture a voltage in the range of 1.3-1.8 volts is applied across cell 21 to remove $O_2$ and disassociate all A gas molecules in volume 40 and a voltage of, for example, 2.6 volts is applied across cell 31 to disassociate all B and C molecules in volume 40. The saturation current across cell 31 would be proportional to the concentration of B plus C in the mixture. In this latter case, B plus C would be the measurement gas and $O_2$ plus A would be the second oxygen containing gas. The voltage at which each of the oxygen containing gases in a mixture disassociate can be obtained by scanning the voltages as would be apparent to one skilled in the art in view of the present disclosure. Effective use of the invention to measure a measurement gas, individually or in total, would depend in part on the difference between the voltages applied across the two cells. If the difference is very small, measurement of the gas would be less effective, i.e., it is more difficult to separate the gases at each of the electrodes. Other factors which influence the effective use of the invention include factors such as type of electrode material (fast electrode processes), physical state (microstructure) of the electrodes, and the geometry of the device. The techniques described herein for measuring the relative amount of, e.g., B plus C in the mixture are similarly applicable to the planar device disclosed herein as would be apparent to one skilled in the art in view of the present disclosure.

The device and method of this invention (including the aspects disclosed herein directed to the planar device and method) can be used in a continuous way (i.e., to continuously monitor the relative amount of an individual gas or a combination of gases in a gas mixture) or in an intermittent (sampling) way. That is, the values of the appropriate individual voltages across the first and second pump cell may be maintained for an extended period of time during which it is desired to measure the relative amount of the measurement gas in the restricted volume, e.g., the humidity in air during the entire operation of an automobile. On the other hand, the determination of one gas need not be done continuously. Measurement of e.g., the humidity of air can be done on a periodic (intermittent) basis. If it is desired to determine the individual concentration of two or more gases in a gas mixture, e.g., the concentration of $CO_2$ in air and also the humidity of the same air sample, the voltages across the first and second pump cells would be alternated, first to that combination which will allow measurement of the $CO_2$ in the air sample (as has been described above) and then to that combination which will allow measurement of the humidity ($H_2O$) in the air (as also has been described above). In the same way, the present invention is capable of measuring the concentration of one oxygen containing gas and also the total of two or more of the oxygen containing gases in the gas mixture. Numerous ways of applying the invention to measure the relative amount of oxygen containing gas in a gas mixture will be apparent to those skilled in the art in view of the present disclosure.

Figure 7:
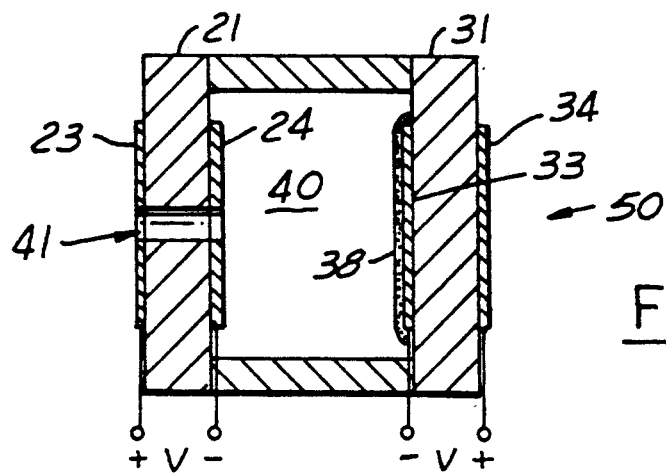
FIG. 7 is a schematic of an electrochemical device for measuring the relative amount of a measurement gas in a gas mixture according to a second embodiment of the present invention.

The device of FIG. 1 operates under the assumption that cell 21 can pump all oxygen entering volume 40 through aperture 41 so that only a measurement gas reaches cell 31, (since aperture 41 is in close proximity to electrode 24 and remote with respect to electrode 33). If this is not the case with the configuration of FIG. 1, the desired condition can be accomplished by modifying the device structure 50 as shown in FIG. 7. In this structure, a porous layer 38 is deposited on top of the inner electrode of cell 31. This porous layer is made from $ZrO_2$ or an inert material (e.g. spinel or aluminum oxide) and acts as a barrier to $O_2$ diffusion so that all $O_2$ is pumped out by cell 21.

Figure 8A:
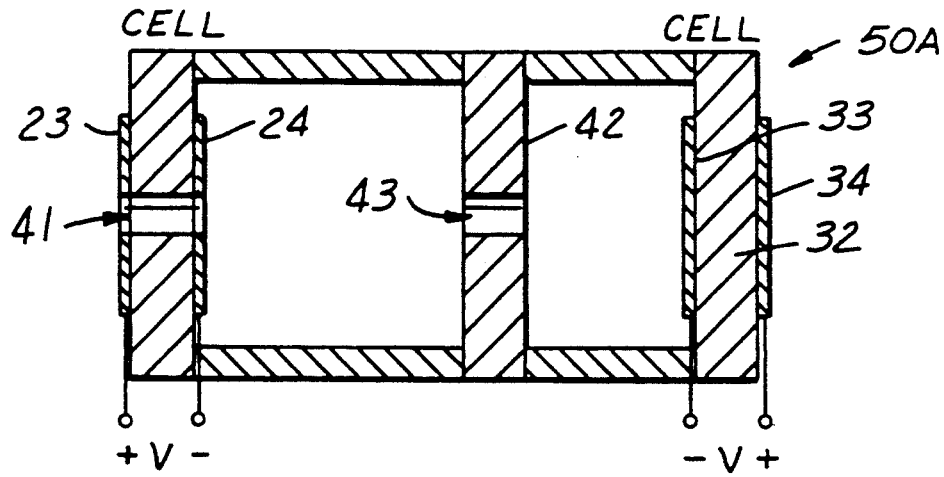
FIGS. 8A and 8B are schematics of electrochemical devices for measuring the relative amount of a measurement gas in a gas mixture according to other embodiments of the present invention.
Figure 8B:
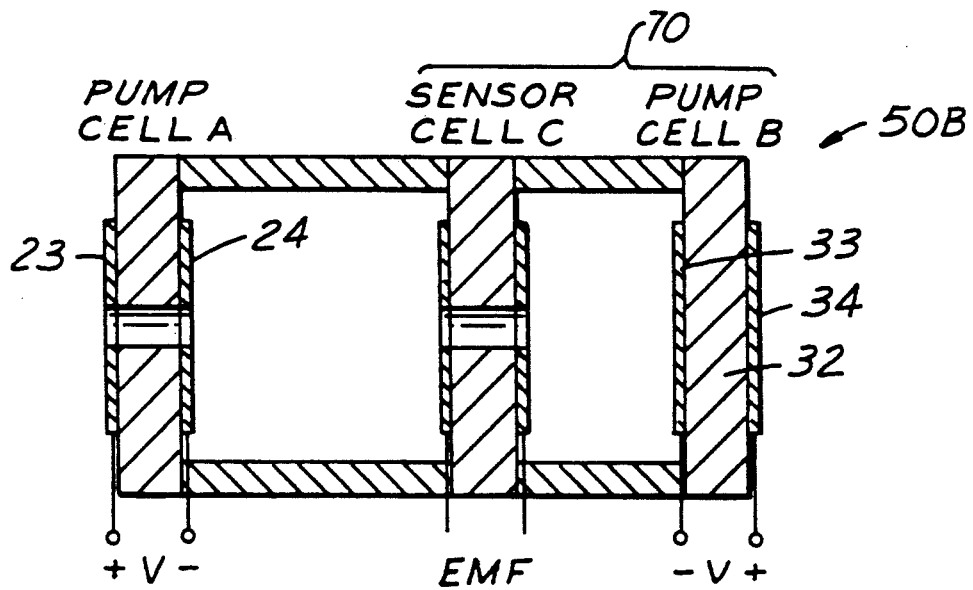

Several other device configurations are possible. According to other embodiments of this invention, the two pumping cells are more strongly decoupled by placing between them barriers to oxygen diffusion. For example, the porous layer in the device of FIG. 7 may be relilaced with a "wall" 42 having an aperture 43 as shown in device 50A of FIG. 8A. Another type of configuration is shown in device 50B of FIG. 8B. Device 50B uses a pump cell to remove the $O_2$ or decompose oxygen containing gases other than the measurement gas and a pump cell/sensor cell structure 70 (similar to the sensor structure described in U.S. Pat. No. 4,272,329 by Hetrick et al) to measure the measurement gas.

Figure 9:
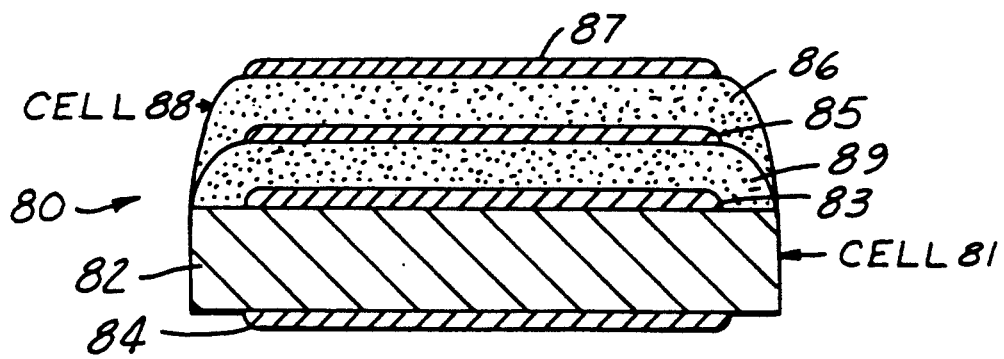
FIG. 9 is a schematic of an electrochemical device having a planar configuration for measuring the relative amount of a measurement gas in a gas mixture according to another embodiment of the present invention.

As disclosed above, the electrochemical device for determining relative amount of the measurement gas can also be made in a planar configuration. FIG. 9 shows one embodiment of a planar device 80 according to this invention. One starts with a dense platelet 82 and deposits porous electrodes 83 and 84 on both sides of platelet 82 to form a first oxygen pump cell 81. Platlet 82 is made from an oxygen ion conducting solid electrolyte such as $ZrO_2$. The electrodes are made of platinum or some other material according to procedures well established in the area of oxygen sensors. A first porous layer 89 made of $ZrO_2$ or an inert material such as spinel or alumina is deposited on top of electrode 83 to form a barrier to diffusion of $O_2$ molecules. A first porous electrode 85 is deposited on first porous layer 89 followed by another porous layer 86 made from an oxygen ion conducting electrolyte such as $ZrO_2$. Finally, a second porous electrode 87 is deposited on top of second porous layer 86. Porous layer 86 and electrodes 85 and 87 form second pump cell 88. The gas mixture communicates with the first porous layer 89, by means of, for example diffusion of the gas mixture into porous layer 89 through its sides. The sides may be exposed or covered with porous electrode material through which the gas mixture may diffuse into the first porous layer 89. The gas mixture may also communicate with the first porous layer 89 by diffusion of the gas mixture into second porous layer 86 and subsequently diffusion of the gas mixture through first porous electrode 85 into first porous layer 89.

An appropriate voltage is applied across second pump cell 88, the second electrode 87 being biased positively, to pump out or decompose oxygen containing gases which can be pumped out or disassociated at voltages lower than that which decompose the measurement gas. This voltage is less than that which is capable of disassociating the measurement gas in the porous parts of the structure. An appropriate voltage is applied across first pump cell 81 to completely disassociate only all of the measurement gas inside the porous layer 89. The saturation current of pump cell 81 is proportional to the relative amount of measurement gas in the gas mixture.

Various modifications and variations will no doubt occur to those skilled in the art to which this invention pertains. For example, the particular construction of the two cell oxygen pumping device may be varied from that disclosed herein. These and all other variations which basically rely on the teachings through which this invention has advanced the art are properly considered within the scope of this invention.

We claim:

1. A method employing an electrochemical oxygen pumping device for measuring the relative amount of a measurement gas consisting essentially of at least one oxygen containing gas in a gas mixture comprising in addition at least a second oxygen containing gas which is capable of being pumped out of said device or disassociated at a voltage less than that which is capable of disassociating said measurement gas, said method comprising the steps of:

providing communication between said gas mixture and a first porous layer of an electrochemical device, which device comprises;

a generally planar first electrochemical oxygen pump cell including a relatively dense platelet with one of a pair of porous electrodes on each of two spaced sides of said platelet, one of said porous electrodes being exposed;

the first porous layer deposited on one of the electrodes of said first pump cell;

a generally planar second electrochemical oxygen pump cell including a first porous electrode, a second porous layer and a second porous electrode deposited successively on said first porous layer;

applying and maintaining a first voltage across said second pump cell to positively bias said second electrode (i) sufficiently to cause substantially all said second oxygen containing gas molecules inside said first porous layer to be pumped out or disassociated by a current flowing through said second pump cell and (ii) insufficiently to disassociate said measurement gas;

applying and maintaining simultaneously with the maintaining of said first voltage, a second voltage across said first pump cell to positively bias the exposed electrode of said first pump cell sufficiently to disassociate only substantially all of said measurement gas molecules inside said first porous layer; and measuring said current flowing through said first pump cell, said current being proportional to the relative amount of said measurement gas in said gas mixture.

2. A method as recited in claim 1, which further comprises measuring said current flowing through said second pump cell, said second pump cell current being proportional to the relative amount of said second oxygen containing gas in said gas mixture.

3. The method as recited in claim 1, further comprising the step of continuously measuring said current flowing through said first pump cell for continuously monitoring said measurement gas in said gas mixture while said first and second applied voltages are maintained.

4. The method as recited in claim 1, further comprising the steps of changing said first and second voltages applied to said first and second pump cells, respectively, for allowing the measurement of a different measurement gas.

* * * * *